(12) United States Patent
Lin et al.

(10) Patent No.: US 9,592,298 B2
(45) Date of Patent: *Mar. 14, 2017

(54) MEDICATION WITH A REDUCED BITTER TASTE PERCEPTION

(71) Applicant: The Procter & Gamble Company, Cincinnati, OH (US)

(72) Inventors: Yakang Lin, Liberty Township, OH (US); Koti Sreekrishna, Mason, OH (US); Jason William Newlon, Lebanon, OH (US); Molly Christine Findley, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/633,160

(22) Filed: Feb. 27, 2015

(65) Prior Publication Data

US 2015/0238612 A1  Aug. 27, 2015

Related U.S. Application Data

(60) Provisional application No. 62/065,843, filed on Oct. 20, 2014, provisional application No. 61/945,437, filed on Feb. 27, 2014.

(51) Int. Cl.
| | |
|---|---|
| *A61K 47/34* | (2006.01) |
| *A61K 31/09* | (2006.01) |
| *A61K 31/167* | (2006.01) |
| *A61K 8/84* | (2006.01) |
| *A61K 31/136* | (2006.01) |
| *A61K 9/00* | (2006.01) |

(52) U.S. Cl.
CPC ............... *A61K 47/34* (2013.01); *A61K 8/84* (2013.01); *A61K 9/0095* (2013.01); *A61K 31/09* (2013.01); *A61K 31/136* (2013.01); *A61K 31/167* (2013.01)

(58) Field of Classification Search
CPC ...................................................... A61K 47/34
See application file for complete search history.

(56) References Cited

U.S. PATENT DOCUMENTS

2013/0243935 A1  9/2013  Barnekow et al.

FOREIGN PATENT DOCUMENTS

| DE | EP 2438907 A2 * | 4/2012 | ............ A61K 8/416 |
| EP | 2438907 A2 | 4/2012 | |
| WO | WO 98/05312 A1 | 2/1998 | |
| WO | WO 9805312 A1 * | 2/1998 | ........... A61K 9/0095 |
| WO | WO 2006/013416 A1 | 2/2006 | |

OTHER PUBLICATIONS

International Search Report and Written Opinion for 13579—PCT/US2015/017895 dated Jun. 15, 2015.
Rhodia: "Mirapol A-15 Product Data Sheet", Sep. 1, 2008, http://dewolfchem.com/wp-content/uploads/2013/08/mirapol-a15.pdf.

* cited by examiner

*Primary Examiner* — Timothy Thomas
(74) *Attorney, Agent, or Firm* — Alexandra S. Anoff

(57) ABSTRACT

A liquid medication with reduced bitterness containing a drug active and polyquaternium-2, polyquaternium-17, and/or polyquaternium-18.

16 Claims, 10 Drawing Sheets

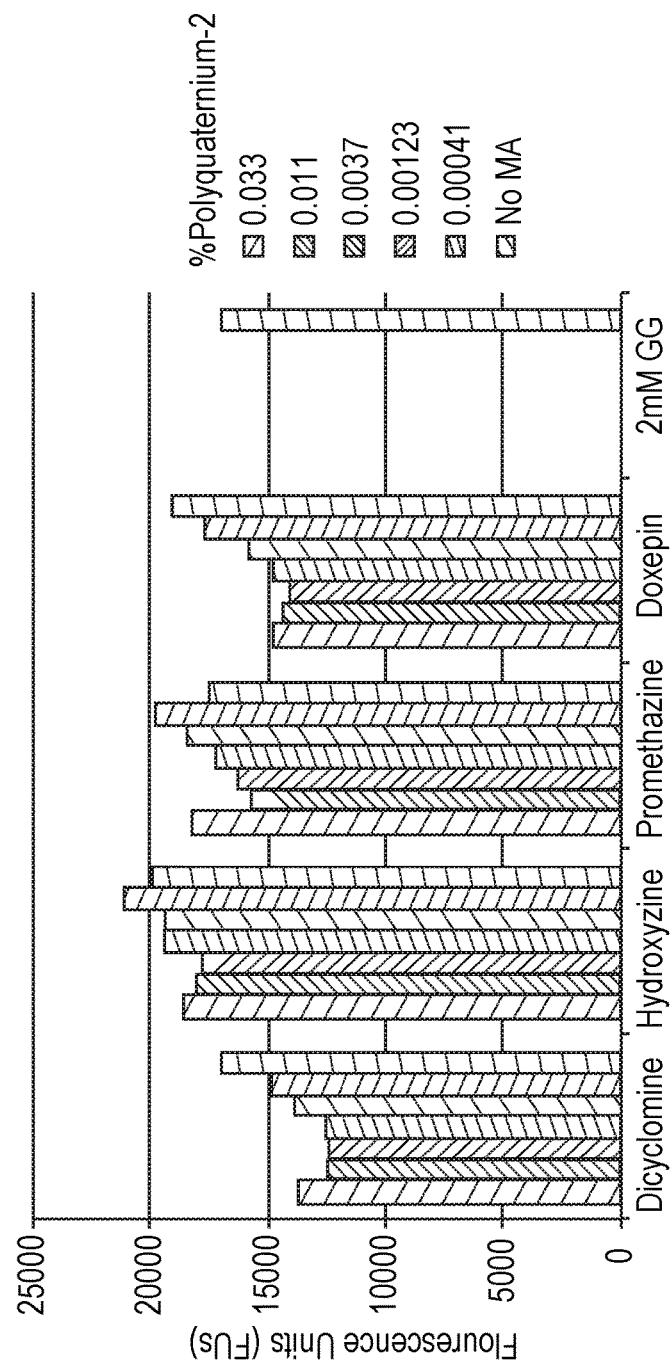

MEDICATION WITH A REDUCED BITTER TASTE PERCEPTION

FIELD OF THE INVENTION

The present invention relates to a liquid medication comprising a low molecular weight polyquaternium to modulate bitterness, more particularly a low level of polyquaternium-2, polyquaternium-17, and/or polyquaternium-18 to modulate bitterness.

BACKGROUND OF THE INVENTION

There are five recognized taste sensations, sweet, salty, sour, bitter, and umami. Many people dislike things that are overly bitter and perceive it is as unpleasant, sharp, or otherwise disagreeable. Bitterness is the most sensitive of the tastes and it is thought to be a defense mechanism to protect the body against ingestion of toxic substances, as a large number of natural bitter compounds are known to be toxic.

However many medications, especially liquid medications, have a bitter taste associated with them due to the drug actives and excipients. Medications often contain flavors and sweeteners to mute the bitterness associated with the actives and excipients. Despite these efforts, many medications still possess an unpleasant taste and/or after taste. This causes some consumers to avoid and/or dread taking medications due to the unpleasant taste.

Thus, there is a need for a medication, in particular a liquid medication, with reduced bitterness.

SUMMARY OF THE INVENTION

A liquid medication with reduced bitterness comprising: (a) a drug active; and (b) a polyquaternium selected from the group consisting of polyquaternium-2, polyquaternium-17, polyquaternium-18, and combinations thereof.

A liquid medication with reduced bitterness comprising: (a) a drug active selected from the group consisting of guaifenesin, phenytoin, omeprazole, cetirizine, jambu, acetaminophen, and combinations thereof; (b) a polyquaternium selected from the group consisting of polyquaternium-2, polyquaternium-17, polyquaternium-18, and combinations thereof; wherein an overall bitterness is reduced by at least about 40% as compared to an identical composition without the polyquaternium as determined by the in vitro Assay for Taste Receptors; and wherein an overall bitterness is less than about 6500 fluorescence units as determined by the in vitro Assay for Taste Receptors.

A dose of liquid medication with reduced bitterness comprising: (a) at least about 200 mg guaifenesin; (b) from about 0.05% to about 0.2% of a polyquaternium selected from the group consisting of polyquaternium-2, polyquaternium-17, polyquaternium-18, and combinations thereof; wherein a Descriptive Profile Panel of in mouth bitter is reduced by at least about 25% as compared to an in mouth bitter of an identical composition without the polyquaternium.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 4A compares the modulation of bitterness of solutions containing an active and a concentration of polyquaternium-2 in an Assay for Taste Receptors;

DETAILED DESCRIPTION OF THE INVENTION

Figure 1A:
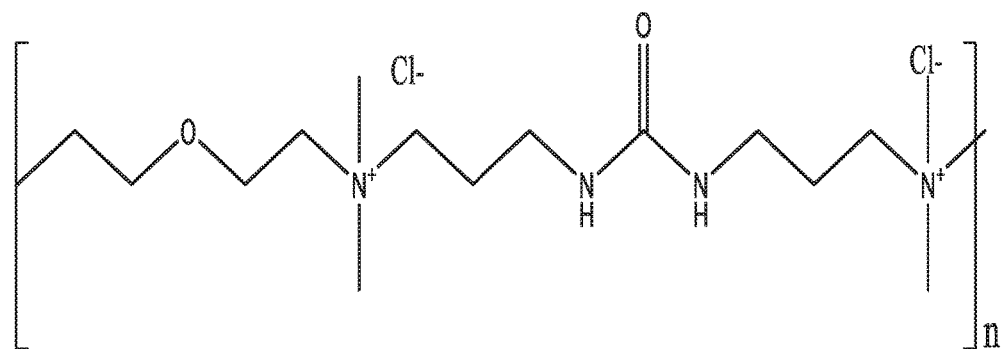
FIG. 1A shows the molecular structure for polyquaternium-2.

Many medications, especially liquid medications, have a bitter taste associated with them due to the drug actives and excipients. It has been surprisingly found that polyquaternium-2 can significantly modulate the bitterness in liquid medications.

Several polymers, including other polyquats, were tested in vitro taste bud cell assays to determine whether they may serve as a bitter blocker. Polyquaternium-2 modulated the bitterness of guaifenesin (GG) in the cell assays better than any other polymer, including the polyquats which have a similar chemical structure. Polyquaternium-17 and/or polyquaternium-18 are structurally analogous to polyquaternium-2 and can be used instead of or in combination with polyquaternium-2.

Although polyquaternium-2 significantly reduced the bitterness of GG, one of the most bitter actives, based on the in vitro assays, it does not modulate the bitterness of all actives to the same extent. For instance, polyquaternium-2 significantly modulated the bitterness of phenytoin, omeprazole, jambu extract and acetaminophen (APAP), but had little effect on bitter actives such as dicyclomine, hydroxyzine, promethazine, doxepin, and diphenhydramine.

Furthermore, it was surprisingly found that polyquaternium-2 modulated bitterness better at the relatively low concentration of about 0.1%, as compared to higher concentrations.

As used herein, "dose" refers to a volume of medication, such as liquid medication, containing an amount of a drug active suitable for administration on a single occasion, according to sound medical practice. A dose can be orally administered. In one example, a dose can be about 30 mL, in another example about 25 mL, in another example about 20 mL, in another example about 15 mL, and in another example about 10 mL. In another example, a dose of liquid medication can be from about 10 mL to about 75 mL, in another example from about 15 mL to about 50 mL, in another example from about 25 mL to about 40 mL, and in another example from about 28 mL to about 35 mL. The concentration of active ingredients can be adjusted to provide the proper doses of actives given the liquid dose size. In one example, the dose is intended to be administered every 4 hours, in another example every 6 hours, in another example every 8 hours, and in another example every 12 hours.

As used herein, "medication" refers to medications, such as pharmaceuticals, including prescription medications, over-the-counter medications, behind-the-counter medications and combinations thereof. In some examples, a medication can be a supplement.

As used herein, the articles "a" and "an" are understood to mean one or more of the material that is claimed or described, for example, "an active" or "a solvent".

The composition the present invention can contain, consist of, or consist essentially of, the essential elements and limitations of the invention described herein, as well as any additional or optional ingredients, components, or limitations described herein or otherwise useful in dosage forms intended for use or consumption by humans.

Figure 1B:
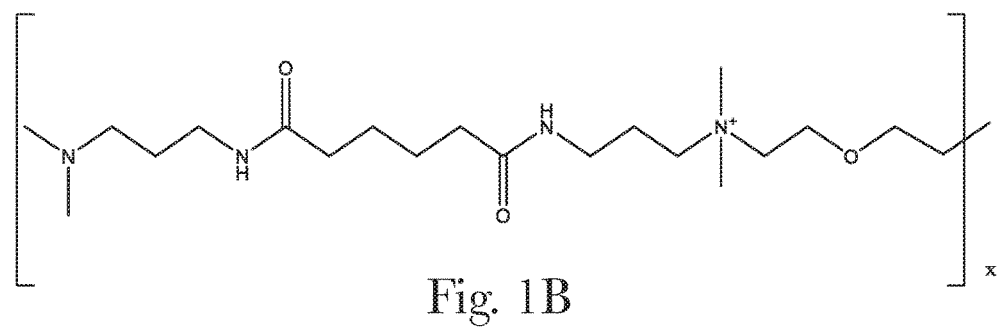
FIG. 1B shows the molecular structure for polyquaternium-17.
Figure 1C:
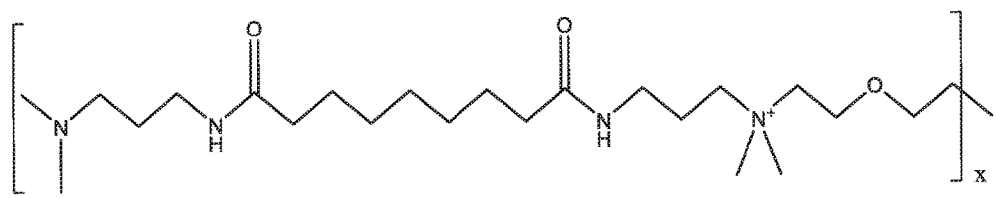
FIG. 1C shows the molecular structure for polyquaternium-18.

It has been found that polyquaternium-2 can be added to compositions, particularly liquid medications, to reduce bitterness. Polyquaternium-2 has the CAS Registry Number 68555-36-2 and the chemical name is Poly[bis(2-chloroethyl) ether-alt-1,3-bis[3-(dimethylamino)propyl]urea] and is commercially available as Mirapol® A 15 (available from Rhodia, Cranbury, N.J.). The molecular structure for polyquaternium-2 is shown in FIG. 1A. Polyquaternium-17 (CAS Registry Number 148506-50-7) and polyquaternium-18 (CAS Registry Number 113784-58-0) are structurally analogous to polyquaternium-2 and can be used in addition to or instead of polyquaternium-2 to modulate bitter. The molecular structure for polyquaternium-17 is shown in FIG. 1B and the molecular structure for polyquaternium-18 is shown in FIG. 1C.

Figure 2:
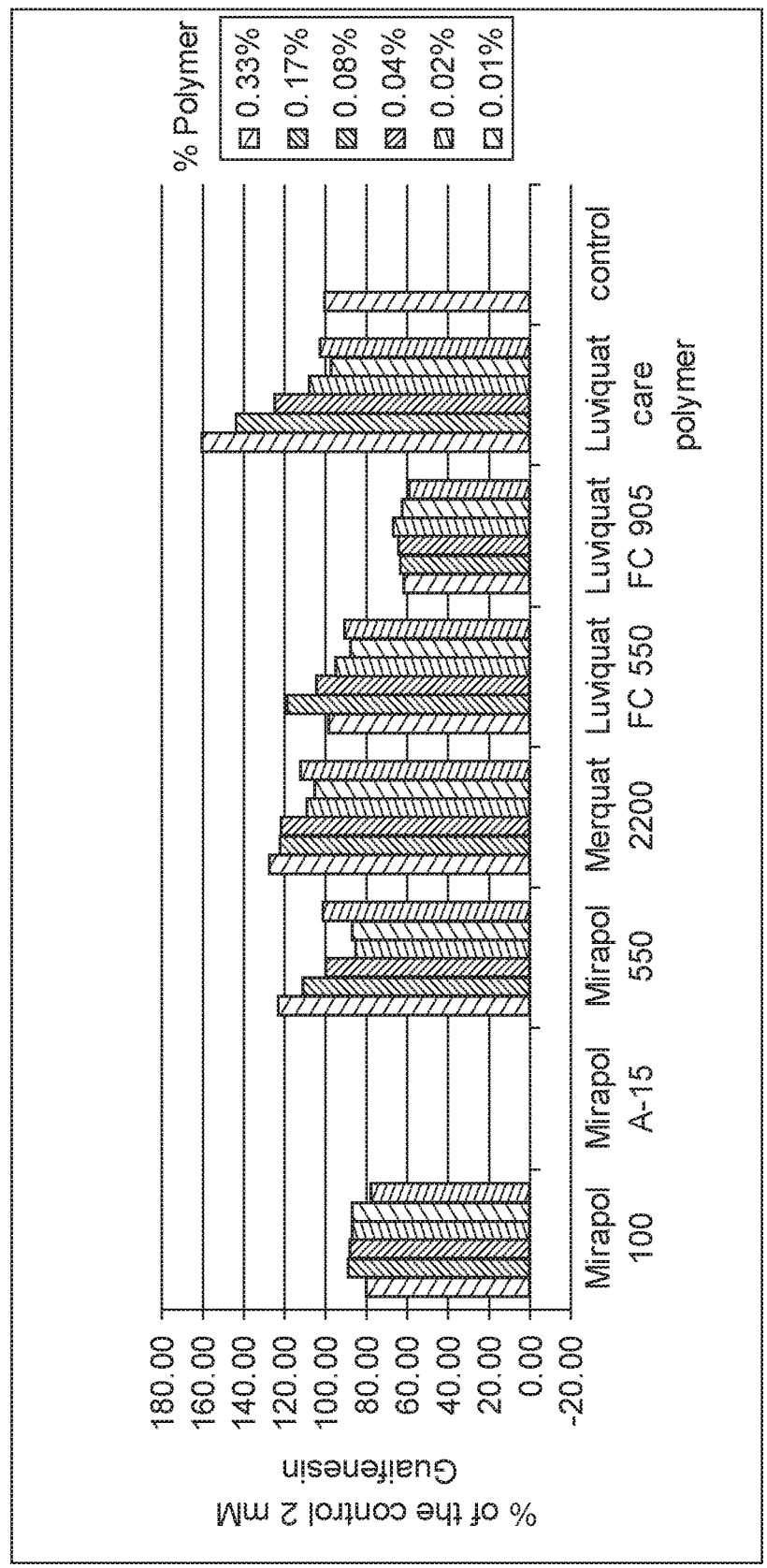
FIG. 2 compares the modulation of bitterness of solutions with different water soluble polymers in an Assay for Taste Receptors.

FIG. 2 compares the modulation of bitterness of a control solution comprising 2 mM guaifenesin (GG) with solutions comprising 2 mM GG and one of seven water soluble polymers at concentrations ranging from 0.33% to 0.01%. The results for FIG. 2 are from an in vitro Assay for Taste Receptors, as described hereafter. The cell cultures and assays provide an in vitro method to screen for bitterness that can mimic an in vivo response.

The water soluble polymers that were tested were as follows at concentrations ranging from 0.01% to 0.33%:
Polyquaternium-6 commercially available as Mirapol® 100 [CAS #26062-79-3] (available from Rhodia, Cranbery, N.J.)
Polyquaternium-2 commercially available as Mirapol® A 15 [CAS #68555-36-2] (available from Rhodia, Cranbury, N.J.)
Polyquaternium-7 commercially available as Mirapol® 550 [26590-05-6] (available from Rhodia, Cranbury, N.J.)
Polyquaternium-7 commercially available as Merquat™ 2200 [CAS #26590-05-6] (available from Lubrizol, Deer Park, Tex.)
Polyquaternium-16 commercially available as Luviquat® FC550 [CAS #95144-24-4] (available from BASF, Florham Park, N.J.)
Polyquaternium D16 commercially available as Luviquat® FC 905 [CAS #95144-24-4] (available from Crescent Company, Islandia, N.Y.)
Polyquaternium-44 commercially available as Luviquat® care polymer [CAS #150599-70-5] (available from BOC Sciences, Shirley, N.Y.)

The taste receptors were activated as described in the Assay for Taste Receptors herein. The observed activation is presented as a % of the control value. The control value is activation by a 2 mM GG solution with no added polymers. The results from this assay showed that only Polyquaternium-2 completely blocked the activation of taste cell receptors by GG. This is especially surprising, since GG is one of the most bitter actives used in liquid medications. Other polymers, including polyquaternium-6 and polyquaternium D16 (Luviquat® 905) also showed some reduction, however the modulation was not dose dependent.

Figure 3:
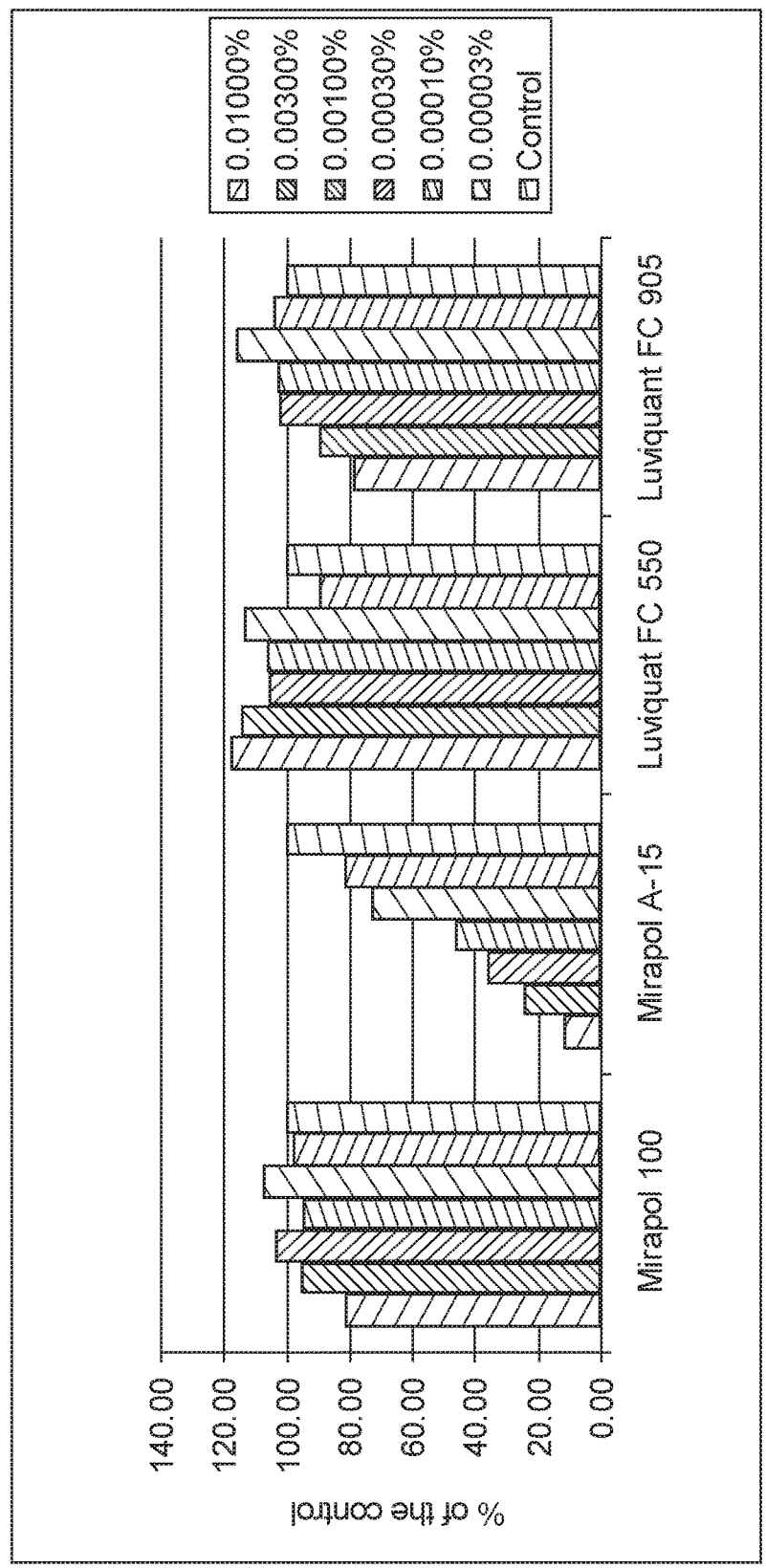
FIG. 3 compares the modulation of bitterness of solutions with different water soluble polymers in an Assay for Taste Receptors.

FIG. 3 compares the modulation of bitterness of a solution comprising 2 mM GG with one of four water soluble polymers at concentrations ranging from 0.01% to 0.00003%. The four water soluble polymers were polyquaternium-6 (Mirapol® 100), polyquaternium-2 (Mirapol® A15), polyquaternium D16 (Luviquat® FC 550), and polyquaternium D16 (Luviquat® FC 905). The same Assay for Taste Receptor Method described herein and for FIG. 2 was used to generate the results for FIG. 3. The lower concentrations of polymer were selected to help further differentiate the potential ability for the polymers to provide bitter blocking in vivo.

Again, polyquaternium-2 provided the greatest reduction in bitterness of the 2 mM GG solution. At 0.01%, the bitterness was reduced to less than 20% of the bitterness of the control. Furthermore, polyquaternium-2 was the only composition that showed dose dependent blocking.

Figure 4B:
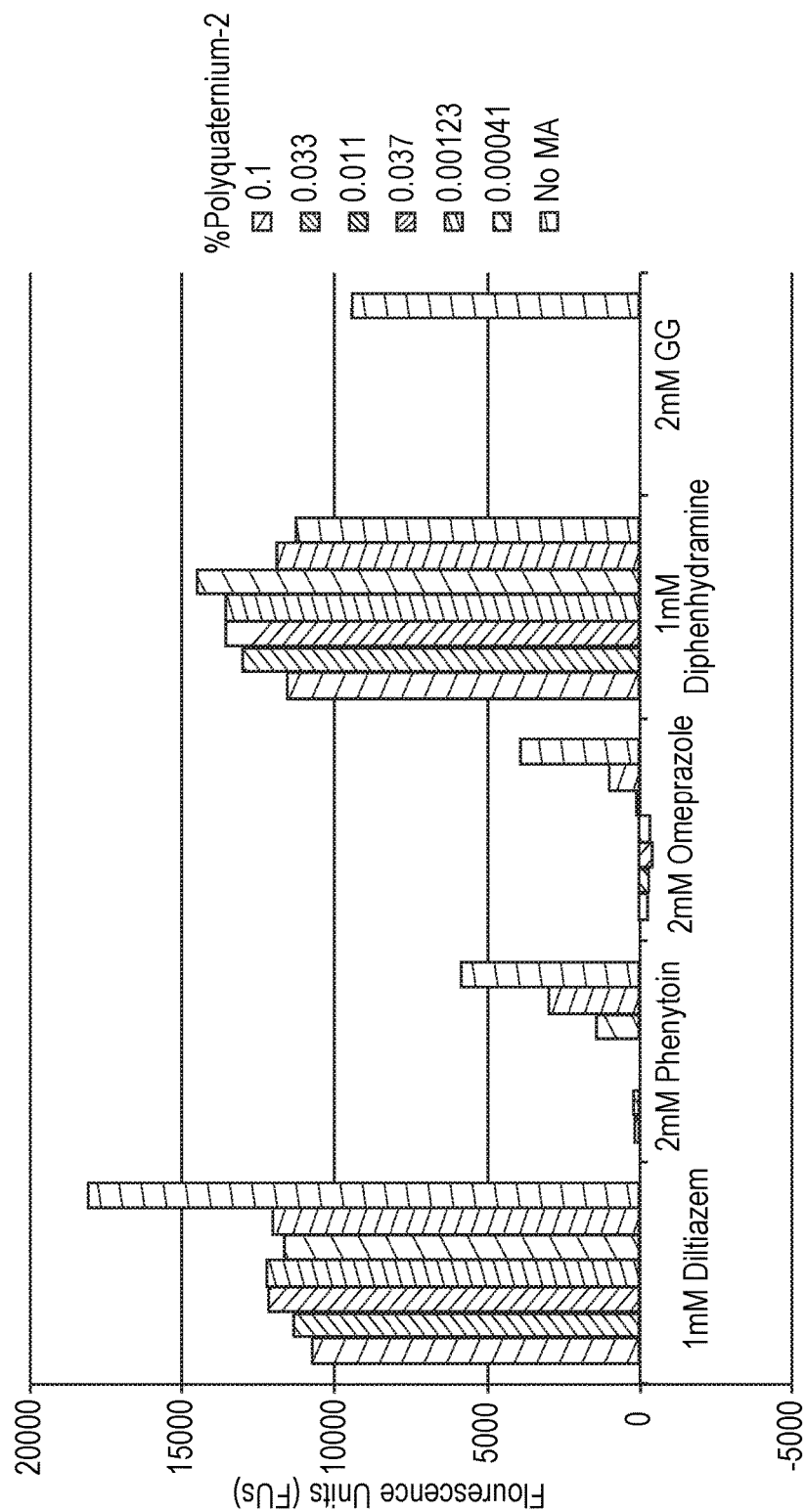
FIG. 4B compares the modulation of bitterness of solutions containing an active and a concentration of polyquaternium-2 in an Assay for Taste Receptors.
Figure 4C:
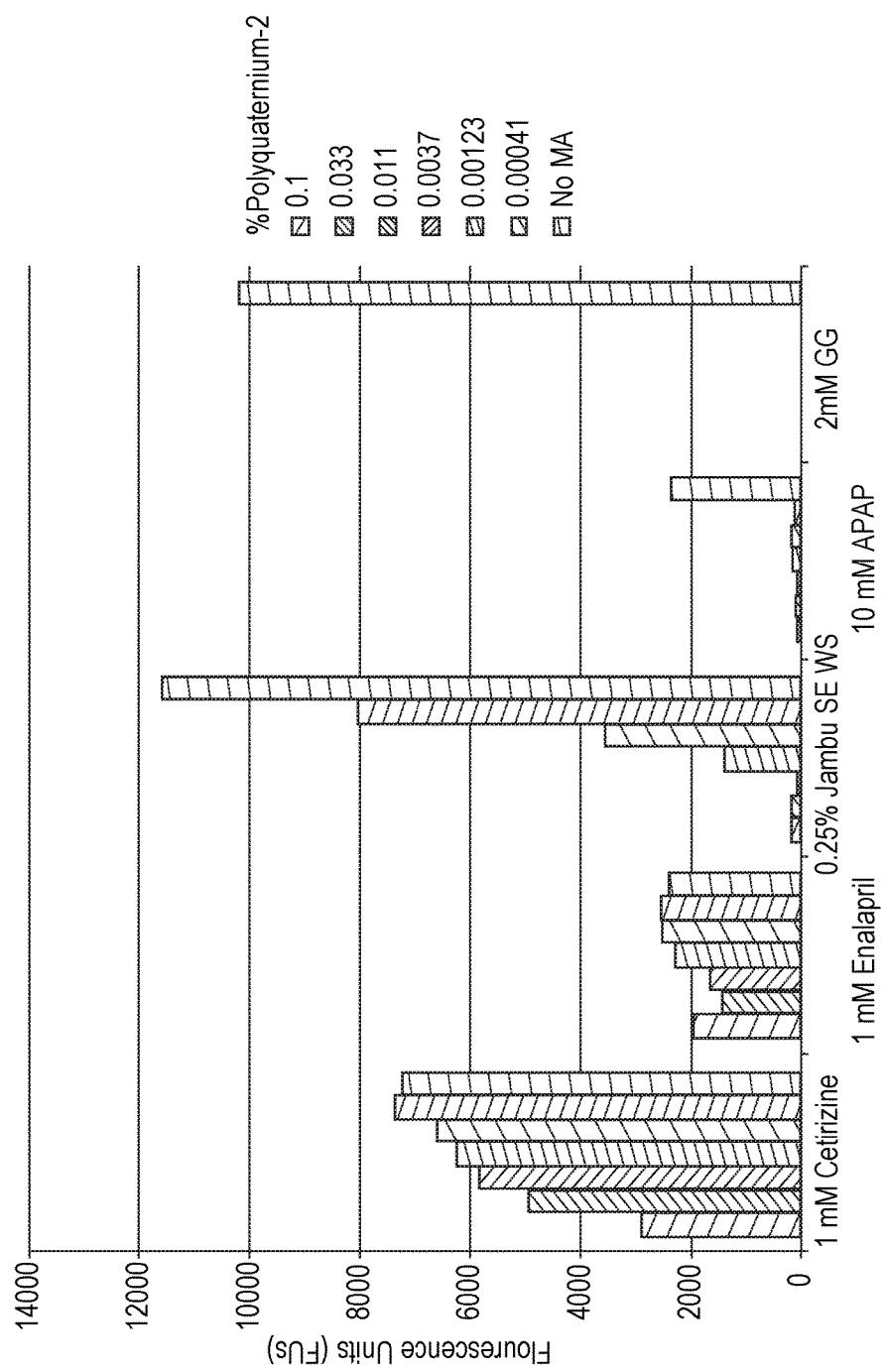
FIG. 4C compares the modulation of bitterness of solutions containing an active and a concentration of polyquaternium-2 in an Assay for Taste Receptors.

Since polyquaternium-2 was effective in blocking the bitterness in the Assay for Taste Receptors, it was desirable to understand if polyquaternium-2 was effective against all bitter actives or select bitter actives. As shown in FIGS. 4A, 4B, and 4C, it was found that polyquaternium-2 only blocked certain bitter drug actives and had little to no effect on others.

FIGS. 4A, 4B, and 4C compare the modulation of bitterness, if any, of solutions containing an active and a concentration of polyquaternium-2. The concentration of polyquaternium-2 ranges from 0.00041% to 0.1%. GG at a concentration of 2 mM without polyquaternium-2 is used as a control. The actives were selected because they are frequently used in medications and are known to be bitter. The results for FIGS. 4A, 4B, and 4C are from an in vitro Assay for Taste Receptors as described hereafter.

FIG. 4A compares the modulation of bitterness, if any, of solutions comprising 250 µM active and a concentration of polyquaternium-2. The actives in FIG. 4A are dicyclomine, hydroxyzine, promethazine, doxepin, and 2 mM GG. FIG. 4A shows that polyquaternium-2 has at best a very weak bitter blocking activity on dicyclomine, hydroxyzine, promethazine, and doxepin. However, FIG. 4A does not show a dose dependent effect and thus polyquaternium-2 is probably not a specific blocker of these actives.

The actives in FIG. 4B are 1 mM diltiazem, 2 mM phenytoin, and 1 mM diphenhydramine Polyquaternium-2 blocked some of the bitterness of diltiazem, but it doesn't show a dose dependent effect and thus polyquaternium-2 is probably not a specific blocker for diltiazem. Polyquaternium-2 strongly blocked the bitterness from phenytoin and omeprazole and polyquaternium-2 had little or no effect on diphenhydramine.

The actives tested in FIG. 4C included 1 mM cetirizine, 1 mM enalapril, 0.25% jambu (*Acmella oleracea*) extract (commercially available as Jambu SE WS from Naturex™, South Hackensack, N.J.), and 10 mM acetaminophen (APAP). Polyquaternium-2 blocked some of the bitterness of cetirizine. Polyquaternium-2 did not show a dose dependent bitter blocking of enalapril. However, polyquaternium-2 shows a strong dose dependent effect on blocking jambu and APAP.

Figure 4D:
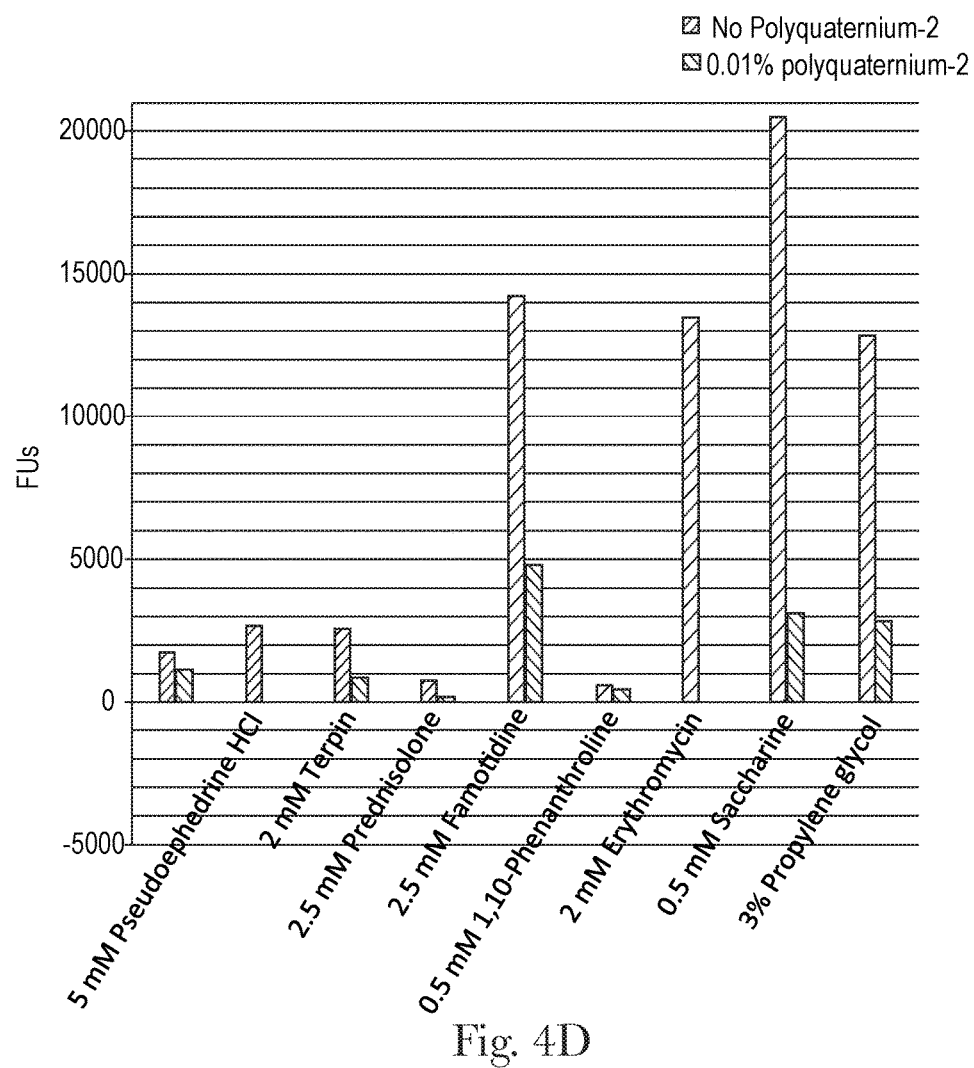
FIG. 4D compares the modulation of bitterness of solutions containing an active or an excipient and a concentration of polyquaternium-2 in an Assay for Taste Receptors.

FIG. 4D compares the modulation of bitterness, if any, of solutions containing an active or an excipient and 0.01% polyquaternium-2 in the in vitro Assay for Taste Receptors as described hereafter. The compositions tested were 5 mM pseudoephedrine hydrochloride, 2 mM terpin, 2.5 mM prednisolone, 2.5 mM famotidine, 0.5 mM 1,10-phenanthroline, 0.5 mM erythromycin, 0.5 mM saccharin, 3% propylene glycol, and 2 mM GG was used as the control. Polyquaternium-2 modulated the bitterness in all of the compositions, including components that were very bitter, like 1,10-phenanthroline, saccharin, and propylene glycol. Surprisingly, polyquaternium-2 completely blocked the bitterness from saccharin and substantially reduced the bitterness of both propylene glycol and 1,10-phenanthroline.

In one example, polyquaternium-2 polyquaternium-17, and/or polyquaternium-18 can reduce the bitterness of a drug active selected from the group consisting of GG, APAP, jambu extract, cetirizine, phenytoin, omeprazol, 1,10-phenanthroline, and combinations thereof.

Figure 5:
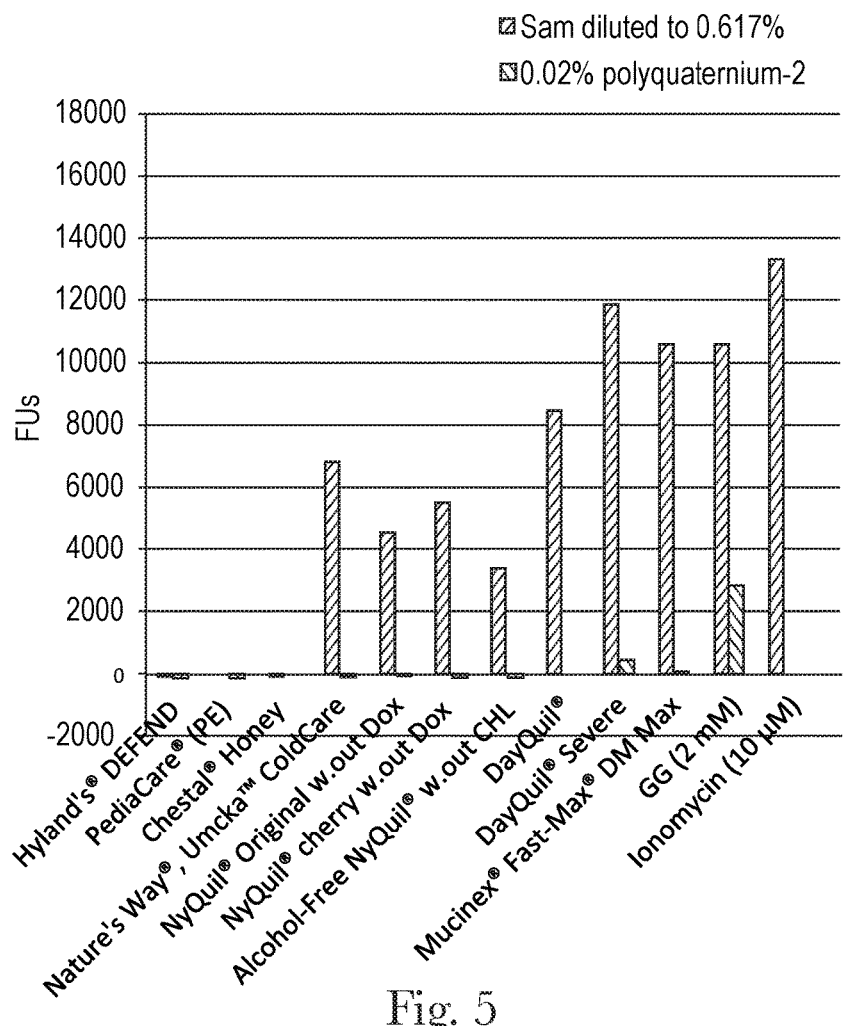
FIG. 5 compares the modulation of bitterness of full formulations containing one or more actives and excipients in an Assay for Taste Receptors.
Figure 6:
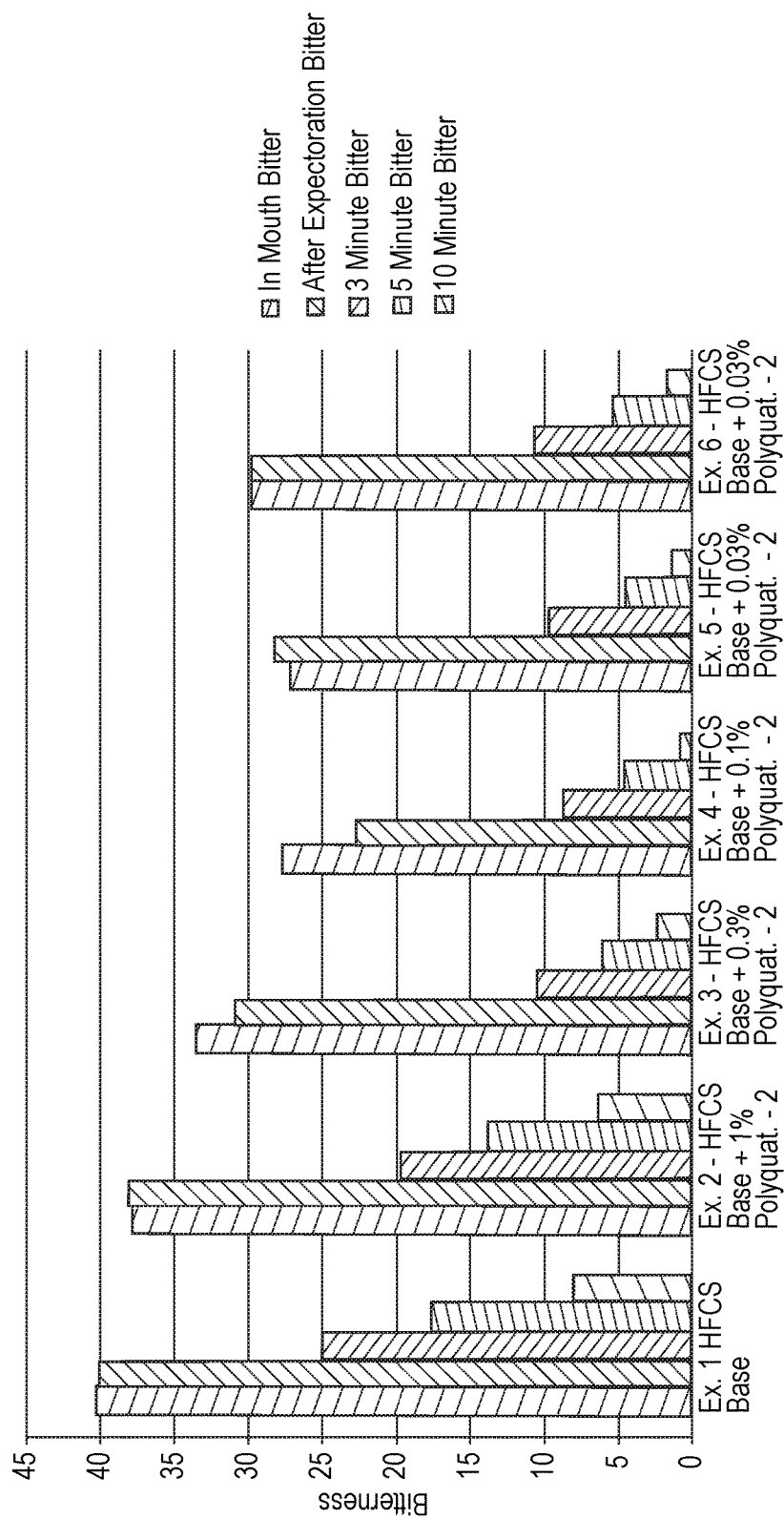
FIG. 6 shows the Descriptive Profile Panel (DPP) bitter intensity of six different compositions containing a high fructose corn syrup (HFCS) base, guaifenesin, and different concentrations of polyquaternium-2.

FIG. 5 compares ten full formulations diluted to 0.617% with the same ten formulations diluted to 0.617% with 0.02% polyquaternium-2 the in vitro Assay for Taste Receptors as described hereafter. The formulations are described in Table 1 below. FIG. 6 also includes a formulation with 2 mM GG and 10 μM Ionomycin, calcium salt, which were both used as controls.

TABLE 1

| Formulation | Dose Size | Active Ingredients per Dose | Excipients |
|---|---|---|---|
| Hyland's ® DEFEND Cold & Cough (Lot # 114220) | 15 mL | *Allium cepa* 6X, Hepar sulfuris calcareum 12X, *Hydrastis canadensis* 6X, Natrum Muriaticum 6X, Phosphorus 12X, *Pulsatilla* 6X, Sulphur 12X | Citric acid, *glycyrrhiza* extract, purified water, sodium benzoate N.F., vegetable glycerine. |
| PediaCare ® Decongestant (Lot # 18263) | 5 mL | Phenylephrine HCl (2.5 mg) | Carboxymethylcellulose sodium, citric acid, edetate disodium, FD&C red #40, flavors, glycerin, sodium benzoate, sodium citrate, sorbitol, sucralose, water |
| Chestal ® Honey (Lot # M0092897) | 2 US tsp (9.9 mL) | Antimonium tartaricum 6C, *Bryonia* 3C, *Coccus cacti* 3C, *Drosera* 3C, *Ipecacuanha* 3C, *Pulsatilla* 6C, *Rumex crispus* 6C, *Spongia tosta* 3C, *Sticta pulmonaria* 3C | Citric acid, honey, purified water, sodium benzoate, sucrose |
| Nature's Way ®, Umcka ® ColdCare, Mint-Menthol Flavor (Lot # 125637) | 7.5 mL | *Pelargonium sidoides* 1X | Alcohol (8.2%), fructose, natural menthol, natural spearmint flavor, purified water, vegetable-source glycerin |
| Nighttime Cold & Flu Relief similar to Nyquil ® without Doxylamine | 30 mL | Acetaminophen (650 mg), and Dextromethorphan HBr (30 mg) | Citric Acid, sodium citrate dihydrate, FD&C Blue #1, Red#40, purified water, saccharin, ace sulfame potassium, sodium, propylene glycol, alcohol, PEG-8, high fructose corn syrup, flavor |
| Nighttime Cold & Flu Relief similar to NyQuil ® cherry flavor without Doxylamine | 30 mL | Acetaminophen (650 mg), and Dextromethorphan HBr (30 mg) | Citric Acid, sodium citrate dihydrate, FD&C Blue #1, Red#40, purified water, saccharin, ace sulfame potassium, sodium, propylene glycol, alcohol, PEG-8, high fructose corn syrup, flavor |
| Nighttime Cold & Flu Relief similar to Alcohol-Free NyQuil ® without Chlorpheniramine | 30 mL | Acetaminophen (650 mg), and Dextromethorphan HBr (30 mg) | Citric Acid, sodium citrate dihydrate, Red#40, flavor, purified water, saccharin, ace sulfame potassium, sodium, propylene glycol, sodium benzoate, Carboxymethylcellulose sodium, PEG-8, high fructose corn syrup |

TABLE 1-continued

| Formulation | Dose Size | Active Ingredients per Dose | Excipients |
| --- | --- | --- | --- |
| DayQuil ® Cold & Flu Relief (Lot # 124917193U) | 30 mL | Acetaminophen (325 mg), Dextromethorphan HBr (10 mg), and Phenylephrine HCl (5 mg) | Citric Acid, FD&C Yellow No. 6, flavor, glycerin, propylene glycol, purified water, saccharin sodium, sodium benzoate, sodium chloride, sodium citrate, sorbitol, sucralose, xantham gum |
| DayQuil ® Severe | 30 mL | Acetaminophen (650 mg), Guaifenesin(400 mg), Dextromethorphan HBr (20 mg), and Phenylephrine HCl (10 mg) | Citric Acid, FD&C Yellow No. 6, flavor, glycerin, propylene glycol, purified water, saccharin sodium, sodium benzoate, sodium chloride, sodium citrate, sorbitol, sucralose, xantham gum |
| Mucinex ® Fast-Max ® DM Max (Lot # 1002471) | 20 mL | Dextromethorphan HBr (20 mg) Guaifenesin (400 mg) | Anhydrous citric acid, dextrose, D&C Red #33, FD&C Red #40, flavors, glycerin, methylparaben, potassium sorbate, propylene glycol, propylparaben, purified water, saccharin sodium, sodium hydroxide, sucralose, xanthan gum |

In the assays of FIG. 6, 0.02% polyquaternium-2 was effective in substantially reducing or completely reducing the bitterness in all of the full formulations. Polyquaternium-2 completely or almost completely reduced the bitter from Nature's Way® Umcka™ ColdCare, the Nighttime Cold & Flu Relief similar to Nyquil® without doxylamine, the Nighttime Cold & Flu Relief similar to Nyquil® cherry flavor without doxylamine, the Nighttime Cold & Flu Relief similar to Alcohol-Free NyQuil® without chlorpheniramine, and DayQuil®. The 0.02% polyquaternium-2 significantly reduced the bitterness of DayQuil® Severe and Mucinex® Fast-Max® DM Max.

In one example polyquaternium-2, polyquaternium-17, and/or polyquaternium-18 can reduce the overall bitterness of a composition by at least about 5% as compared to an identical composition without the polyquaternium-2, polyquaternium-17, and/or polyquaternium-18 as determined by the in vitro Assay for Taste Receptors as described hereafter, in another example by at least about 10%, in another example by at least about 20%, in another example by at least about 30%, in another example by at least about 40%, in another example by at least about 50%, in another example by at least about 60%, in another example by at least about 65%, in another example by at least about 70%, in another example by at least about 75%, in another example by at least about 80%, in another example by at least about 85%, in another example by at least about 90%, in another example at least about 93%, in another example at least about 95%, in another example by at least about 97%, in another example by at least about 98%, in another example by at least about 99% and in another example by at least about 100%.

In another example, polyquaternium-2, polyquaternium-17, and/or polyquaternium-18 can reduce the overall bitterness of a composition as compared to an identical composition without the polyquaternium-2, polyquaternium-17, and/or polyquaternium-18 as determined by the in vitro Assay for Taste Receptors as described hereafter. In another example, polyquaternium-2, polyquaternium-17, and/or polyquaternium-18 can reduce the overall bitterness of a composition as compared to a composition that contains GG and does not contain polyquaternium-2, polyquaternium-17, and/or polyquaternium-18 as determined by the in vitro Assay for Taste Receptors as described hereafter.

In another example, the composition can have an overall bitterness of less than about 9000 fluorescence units (FUs) as determined by the in vitro Assay for Taste Receptors as described hereafter, in another example less than about 8500 FUs, in another example less than 8000 FUs, in another example less than 7500 FUs, in another example less than about 7000 FUs, in another example less than about 6500 FUs, in another example less than about 6000 FUs, in another example less than about 5500 FUs, in another example less than about 5000 FUs, in another example less than about 4500 FUs, in another example less than about 4000 FUs, in another example less than about 3500 FUs, in another example less than about 3000 FUs, in another example less than about 2500 FUs, in another example less than about 2000 FUs, in another example less than about 1500 FUs, in another example less than about 1000 FUs, in another example less than about 750 FUs, in another example less than about 500 FUs, in another example less than about 350 FUs, in another example less than about 300 FUs, in another example less than about 250 FUs, in another example less than about 200 FUs, in another example less than about 150 FUs, in another example less than about 100 FUs, and in another example less than about 50 FUs.

FIG. 6 compares the bitterness, as determined by the DPP panel, of the examples described in the table below. The high fructose corn syrup (HFCS) base contains 46.7% HFCS stock, 5.9% PEG-400 (polyethylene glycol 400), 8.6% propylene glycol, 7.4% ethanol, and 30.07% water. Excipients, including propylene glycol, can be bitter and the polyquaternium-2 can block the bitterness of the excipients in the HFCS base.

| Example | High Fructose Corn Syrup Base | Polyquaternium-2 |
| --- | --- | --- |
| 1 | q.s. | 0% |
| 2 | q.s. | 1% |
| 3 | q.s. | 0.3% |
| 4 | q.s. | 0.1% |
| 5 | q.s. | 0.03% |
| 6 | q.s. | 0.01% |

Each panelist sampled 10 mL of each example using a "swish-and-spit" approach and rated the formulation for perceived bitter intensity. The DPP panel includes panelists that are trained and validated in Spectrum™ Descriptive Analysis methodology and evaluate bitterness on a 60 point scale.

It was surprisingly found that the Example 4, which contained 0.1% polyquaternium-2 was less bitter than Examples 2 and 3, which had higher levels of Polyquaternium-2. Examples 5 and 6 were also less bitter than Examples 2 and 3 and may still be acceptable to consumers.

Figure 7:
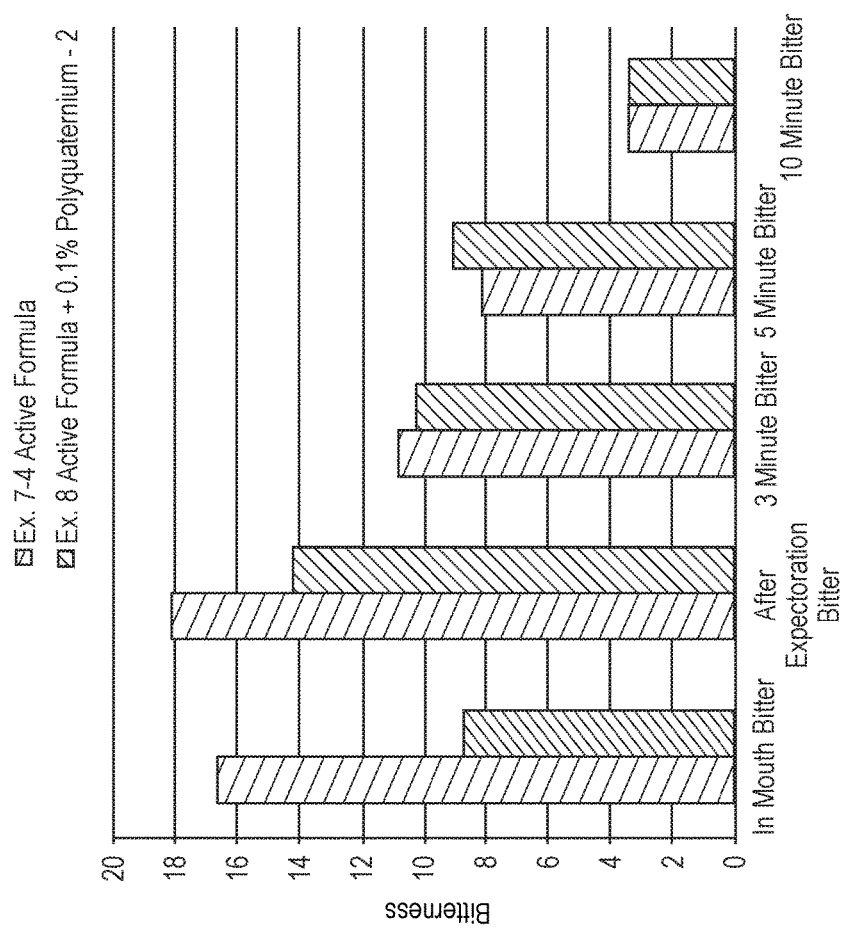
FIG. 7 shows the Descriptive Profile Panel (DPP) bitter intensity of two examples that both contain four actives and one example contains polyquaternium-2.

FIG. 7 compares the bitterness, as determined by the DPP panel, of the following examples:

Example 7 was commercially available DayQuil® Severe (Lot #3308171931, expiration date October 2015) which contains four actives: APAP (216.67 mg per 10 mL), GG (133.33 mg per 10 mL), phenylephrine HCl (PE) (3.33 mg per 10 mL), and dextromethorphan (DXM) (6.67 mg per 10 mL). DayQuil® Severe also contains the following excipients: citric acid, FD&C Yellow No. 6, flavor, glycerin, propylene glycol, purified water, saccharin sodium, sodium benzoate, sodium chloride, sodium citrate, sorbitol, sucralose, xanthan gum Example 8 was the DayQuil® Severe of Example 7 with the addition of 0.1% polyquaternium-2.

The DPP panel for FIG. 7 was conducted according to the procedure described herein for FIG. 6. Polyquaternium-2 reduced the overall bitterness in mouth, after expectoration, and at three minutes. The in mouth bitter was reduced by about 50% and the after expectoration bitter was reduced by over 10%. The three minute bitter was only reduced slightly and there was not a noticeable difference in bitterness after ten minutes. However, it can be most important to reduce the bitterness when the composition is in the mouth and immediately after it has been expectorated because this is the time when the composition is most bitter and unpleasant to the consumer.

In one example, the DPP in mouth bitter is reduced by at least about 5% as compared to the in mouth bitterness of an identical composition without polyquaternium-2, polyquaternium-17, and/or polyquaternium-18, in another example by at least about 10%, in another example by at least about 15%, in another example by at least about 20%, in another example by at least about 25%, in another example by at least about 35%, in another example by at least about 40%, in another example by at least about 45%, and in another example by at least about 50%. In one example, the DPP after expectoration bitter is reduced by at least about 4% as compared to the in mouth bitterness of an identical composition without polyquaternium-2, polyquaternium-17, and/or polyquaternium-18, in another example by at least about 4%, in another example by at least about 10%, in another example the DPP after expectoration bitterness by at least about 15%, in another example by at least about 18%, in another example by at least about 20%, and in another example by at least about 22%.

Polyquaternium-2, polyquaternium-17, and/or polyquaternium-18 can be added to compositions, in particular liquid pharmaceutical compositions. In one example, the composition contains from about 0.01% to about 1% polyquaternium-2, in another example from about 0.03% to about 0.3%, in another example from about 0.05% to about 0.2%, in another example from about 0.07% to about 0.15%, in another example from about 0.08% to about 0.13%, and in another example from about 0.09% to about 0.11. In one example, the composition can contain about 0.1% polyquaternium-2. In another example, the composition can contain less than about 1% polyquaternium-2, in another example less than about 0.5%, in another example less than about 0.3%, in another example less than about 0.2%, in another example less than about 0.15%, and in another example less than about 0.12%.

The compositions can include a variety of orally administered dosage forms. Non-limiting examples of dosage forms can include a liquid medication, particles suspended in a liquid formulation, a solid in a gelatin or foam, or a solid dose in the form of a tablet, powder, granules, pellets, microspheres, nanospheres, beads, or nonpareils, and combinations thereof. In one example, the dosage form is a liquid medication. Dosage forms can be orally administered and can be swallowed immediately, slowly dissolved in the mouth, or chewed.

In one example, polyquaternium-2, polyquaternium-17, and/or polyquaternium-18 can be added to a medication intended for use by children. Children can be especially sensitive to bitter tastes and adding polyquaternium-2, polyquaternium-17, and/or polyquaternium-18 can make bitter medicines more palatable.

Non-limiting examples of additional solvents can include water, ethanol, glycerol, propylene glycol, polyethylene glycol 400, polyethylene glycol 200, and mixtures thereof. In one example the medication comprises from about 40% to about 95% solvent, in another example from about 50% to about 80% solvent, and in another example from about 55% to about 60% solvent, and in another example from about 68% solvent to about 72% solvent.

In one example, the medication can contain water and propylene glycol. In one example, the medication comprises from about 15% to about 80% water, in another example from about 25% to about 75% water, in another example from about 40% to about 70% water, in another example from about 35% to about 45% water, and in another example from about 57% to about 66% water. In another example, the medication can contain from about 1% to about 10% propylene glycol, in another example from about 2% to about 8% propylene glycol, and in another example from about 3% to about 6% propylene glycol. In another example, the medication can contain from about 5% to about 40% propylene glycol, in another example from about 15% to about 35% propylene glycol, and in another example from about 20% to about 30% propylene glycol. In another example, the medication can comprise from about 1% to about 15% ethanol, in another example from about 3% to about 12% ethanol, and in another example from about 6% to about 10% ethanol.

The compositions can comprise a sweetener to provide sweetness and taste masking of the actives and excipients that provide a bitter character. In one example, the composition comprises from about 2% to 25% sweetener, in another example from about 5% to 20% sweetener, in another example from about 7% to 15% sweetener, and in another example from about 8% to 12% sweetener. Non-limiting examples of sweeteners can include nutritive sweeteners, sugar alcohols, synthetic sugars, high intensity natural sweeteners, and combinations thereof. Non-limiting examples of nutritive sweeteners can include fructose, galactose, and combinations thereof. In one example, the sweetener can be high fructose corn syrup.

Non-limiting examples of sugar alcohols can include xylitol, sorbitol, mannitol, maltitol, lactitol, isomalt, erthritol, glycerin, and combinations thereof. In one example the composition can comprise from about 1% to about 30% sugar alcohol, in another example from about 5% to about 28% sugar alcohol, in another example about 10% to about 25% sugar alcohol, and in another example about 15% to about 23% sugar alcohol. In one example the composition comprises from about 5% to about 20% sorbitol, in another example from about 7% to about 18% sorbitol, and in another example from about 10% to about 15% sorbitol. In another example, the composition comprises from about 3% to about 15% glycerin, in another example from about 5% to about 10% glycerin, and in another example from about 7% to about 9% glycerin.

Non-limiting examples of synthetic sweeteners can include sodium saccharin, acesulfame potassium, sucralose, aspartame, monoammonium glycyrrhizinate, neohesperidin dihydrochalcone, thaumatin, neotame, cyclamates, and mixtures thereof. In one example the composition can comprise from about 0.01% to about 0.5% artificial sweetener, in another example from about 0.1% to about 0.3% artificial sweetener, and in another example about 0.15% to about 0.25% artificial sweetener.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof.

The liquid composition can optionally include one or more sensates. Non-limiting examples of sensates can include cooling sensates, warming sensates, tingling sensates, and combinations thereof. Sensates can useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxy-propane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International., cis & trans p-Menthane-3,8-diols(PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl(2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerol acetal, Peppermint oil, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool™ 180 (N-(4-cyanomethylphenyl)-ρ-menthanecarboxamide)), and combinations thereof. In one example, the composition can comprise from about 0.005% to about 1% cooling sensate, in another example from about 0.05% to about 0.5% cooling sensate, and in another example from about 0.01% to about 0.25% cooling sensate.

In one example, the cooling sensate can be EverCool™ 180 available from Givaudan of Cincinnati, Ohio, as a 5% solution of N-(4-cyanomethylphenyl)-ρ-menthanecarboxamide in a flavoring ingredient cool white grape, or as a 7.5% solution of N-(4-cyanomethylphenyl)-ρ-menthanecarboxamide in a flavor ingredient such as spearmint or peppermint.

Non-limiting examples of warming sensates can include TK 1000, TK 1 MM, Heatenol—Sensient Flavors, Optaheat—Symrise Flavors, Cinnamon, Capsicum, Capsaicin, Curry, FSI Flavors, Isobutavan, Nonivamide 60162807, Hotact VEE, Hotact 1MM, piperine, optaheat 295 832, optaheat 204 656, optaheat 200 349, and combinations thereof. Warming sensates can be present from about 0.005% to about 2%, in another example from about 0.01% to about 1%, and in another example from about 0.1% to about 0.5%.

Non-limiting examples of tingling sensates can include sichuan pepper, hydroxy alpha sanshool, jambu extracts, spilanthol, and combinations thereof. In one example, tingling sensates can be present from about 0.005% to about 1%, in another example from about 0.01% to about 0.5%, and another example from about 0.015% to about 0.3%.

The composition can comprise a flavoring ingredient. When present, flavoring ingredients are generally used in the compositions at levels of from about 0.001% to about 8%, by weight of the composition.

Additional non-limiting examples of flavoring ingredients can include peppermint oil, corn mint oil, spearmint oil, oil of wintergreen, clove bud oil, cassia, sage, parsley oil, marjoram, lemon, lime, orange, mango, cis-jasmone, 2,5-dimethyl-4-hydroxy-3(2H)-furanone, 5-ethyl-3-hydroxy-4-methyl-2(5H)-furanone, vanillin, ethyl vanillin, propenyl guaethol, heliotropine, 4-cis-heptenal, diacetyl, methyl-ρ-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavouring ingredients that are saturated or contain stable aromatic rings or ester groups. In one example, the composition comprises from about 0.01% to about 1% flavoring ingredients, in another example from about 0.05% to about 0.5% flavoring ingredients, and in another example from about 0.1% to about 0.3% flavoring ingredients.

The composition can optionally include one or more salivation agents. Non-limiting examples of salivation agents include formula (I):

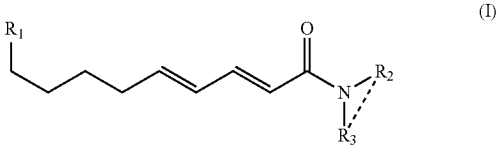

wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula —$(CH_2)_n$— wherein n is 4 or 5, and combinations thereof.

In an embodiment, the salivating agent comprises a material wherein $R_2$ is 2-methyl-1-propyl and $R_3$ is hydrogen, in another embodiment the salivating agent comprises a material wherein $R_1$ is C1 n-alkyl, $R_2$ is 2-methyl-1-propyl and $R_3$ is hydrogen. In another embodiment, the salivating agent comprises trans-pellitorin, a chemical having a structure according to formula (II):

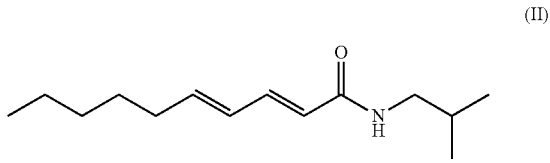 [SMILES: CCCCC/C=C/C=C/C(=O)NCC(C)C]

In another embodiment, the salivation agent can include sodium bicarbonate, sodium chloride, trans-pellitorin, and combinations thereof. In one example, salivation agents can be present from about 0.05% to about 2%, in another embodiment from about 0.1% to about 1%, and in another example from about 0.25%% to about 0.75%.

The liquid composition can be any color. Non-limiting examples of colors can include red, green, amber, orange, yellow, blue, pink, violet, turquoise, and combinations thereof. In one example, the composition is green. In another example, the liquid composition is clear.

The composition can also comprise a dye that provides the color. Non-limiting examples dyes that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. In one example, the composition comprises from about 0.001% to about 0.1% dye, in another example from about 0.002% to about 0.05% dye, and in another example form about 0.003% to about 0.01% dye.

In one example, the composition comprises a buffer. The buffer can help maintain a constant pH within the liquid composition. In one example the liquid composition comprises from about 0.05% to about 2% buffer, in another example from about 0.1% to about 1% buffer, in another example from about 0.15% to about 0.5% buffer, and in another example from about 0.18% to about 0.25% buffer. Buffers can include acetate buffers, citrate buffers, and phosphate buffers. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, and phosphoric acid.

In one example, the composition comprises a preservative. In one example the liquid composition comprises from about 0.01% to about 1% preservative, in another example from about 0.05% to about 0.5% preservative, in another example from about 0.07% to about 0.3% preservative, and in another example from about 0.08% to about 0.15% preservative. Non-limiting examples of preservatives can include benzalkonium chloride, ethylenediaminetetraacetic acid (EDTA), benzyl alcohol, potassium sorbate, parabens, benzoic acid, sodium benzoate, and mixtures thereof.

In one example, the composition comprises a thickener. In one example the liquid composition comprises from 0.01% to 3% thickener, in another example 0.05% to 1.5% thickener, in another example 0.1% to 0.75% thickener, and in another example 0.12% to 0.3% thickener. Non-limiting examples of thickeners can include xanthan gum, carrageenan, polyacrylic acid, polyvinylpyrrolidone, cellulosic polymers including carboxymethycellulose, hydroxethylcellulose, hydroxymethylcellulose, and hydroxypropylmethylcellulose, and combinations thereof.

The liquid compositions can comprise one or more drug actives. In one example, the drug actives can be immediate release drug actives, extended release drug actives, or delayed release drug actives. In one example, the drug active can be formulated as particles and in another example the active can be formulated as coated beads.

In one example, the drug active is a multi-symptom relief (MSR) cold/flu active which can be used to treat one or more cold/flu symptoms. MSR cold/flu actives can be used to treat a variety of cold/flu symptoms including nasal congestion, runny nose, sneezing, headache, dry cough, sore throat, sinus pressure or pain, chest congestion, muscle aches/pains, wet/chesty cough, fever, and combinations thereof. MSR cold/flu actives can include decongestants, expectorants, antihistamines, antitussives, pain relievers, and combinations thereof.

In one example, MSR cold/flu actives can be formulated for daytime use or nighttime use. In one example, the liquid medication comprises instructions that direct a user to ingest the medication at night before bedtime.

Non-limiting examples of expectorants can include guaifenesin, ambroxol, bromhexine, and combinations thereof. In one example, the expectorant can be guaifenesin. In one example a dose can comprise 200 mg of guaifenesin and in another example 400 mg of guaifenesin.

Non-limiting examples of antihistamines can include chlorpheniramine, desloratadine, levocetirizine, diphenydramine, doxylamine succinate, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenydramine, tranilast, carbinoxamine, traxanox, chlorphenoxamine, diphenylpyaline, embramine, p-methyldiphenydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, phenylephrine (PE), pseudophedrine (PSE) and combinations thereof.

In one example the liquid composition can comprise from about 0.01% to about 0.1% antihistamine, in another example from about 0.02% to about 0.07% antihistamine, and in another example from about 0.03% to about 0.05% antihistamine. In one example, the antihistamine can be doxylamine succinate and a dose of liquid medication can contain 12.5 mg doxylamine succinate. In another example, the antihistamine can be chlorpheniramine. In one example a dose can contain 2 mg of chlorpheniramine and in another example a dose can contain 4 mg of chlorpheniramine. In another example, the antihistamine can be PE. In one example a dose can contain 5 mg PE, in another example 10 mg PE, and in another example 20 mg PE. In another example, the antihistamine can be PSE. In one example a dose can contain 120 mg PSE and in another example 30 mg PSE.

Non-limiting examples of antitussives can include DXM, codeine, chlophedianol, levodropropizine, and combinations thereof. In one example the liquid medication can comprise from about 0.01% to about 0.2% antitussive, in another example from about 0.025% to about 0.1%, and in another example from about 0.04% to about 0.075% antitussive. In one example the antitussive can be selected from the group consisting of DXM, chlophedianol, and combinations thereof. In one example a dose can comprise 15 mg DXM, in another example 20 mg DXM, and in another example 30 mg DXM. In another example a dose can comprise 12.5 mg chlophedianol.

Non-limiting examples of pain relievers can include APAP, ibuprofen, ketoprofen, diclofenac, naproxen, aspirin, and combinations thereof. In one example the liquid medication can comprise from about 0.5% to about 3.5% pain reliever, in another example from about 1% to about 3% pain reliever, and in another example from about 1.5% to about 2% pain reliever. In one example the pain relievers can include APAP, ibuprofen, naproxen, or combinations thereof. In one example a dose can comprise 325 mg to 500 mg APAP, in another example 200 mg ibuprofen, and in another example, 200 mg naproxen.

In one example, the liquid medication can further comprise a stimulant such as caffeine.

In one example, the liquid medication can comprise one or more MSR cold/flu actives, in another example two or more MSR cold/flu actives, in another example three or more MSR cold/flu actives, and in another example four or more MSR cold/flu actives. In one example, the liquid medication can comprise exactly one MSR cold/flu active, in another example exactly two MSR cold/flu actives, in another example exactly three MSR cold/flu actives, and in another example exactly four MSR cold/flu actives. In one example the liquid medication can comprise APAP, doxylamine succinate, DXM, and PE.

In one example, the active can be a plant-derived materials. As used herein, non-limiting examples of plant-derived materials can include those used in traditional native American, Chinese, Aryuvedic and Japanese medicine, including flowers, leaves, stems and roots of plants as well as extracts and isolated active components from the flower, leaves, stems, and roots of plants. Plant and Animal based oils and esters such as Omega-3-fatty acids and alkyl esters thereof; Vitamins (including but not limited to provitamin and all forms of Vitamins C, D, A, B, E, and combinations thereof). Fibers: Non-limiting examples of fibers and analogous carbohydrate polymers can include pectins, psyllium, guar gum, xanthan gum, alginaes, gum arabic, fructo-oligosaccharides, inulin, agar, beta-glucans, chitins, dextrins, lignin, celluloses, non-starch polysaccharides, carrageenan, reduced starch, and mixtures and/or combinations thereof; Prebiotics: Non-limiting examples of prebiotics suitable for use in the compositions and methods can include psyllium, fructo-oligosaccharides, inulin, oligofructose, galacto-oligosaccharides, isomalto-oligosaccharides, xylo-oligosaccharides, soy-oligosaccharides, gluco-oligosaccharides, mannan-oligosaccharides, arabinogalactan, arabinxylan, lactosucrose, gluconannan, lactulose, polydextrose, oligodextran, gentioligosaccharide, pectic oligosaccharide, xanthan gum, gum arabic, hemicellulose, resistant starch and its derivatives, reduced starch, and mixtures and/or combinations thereof. Probiotics: Non-limiting examples of probiotic bacteria suitable for use herein can include strains of *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Lactobacillus brevis, Lactobacillus paracasei, Lactobacillus gasseri, Pediococcus cerevisiae, Bifidobacterium longum, Bifidobacterium infantis, Bifidobacterium adolescentis, Bifidobacterium bifidum, Bifidobacterium animalis, Bifidobacterium pseudolongum, Bifidobacterium thermophilum, Bifidobacterium lactis, Bifidobacterium bulgaricus, Bifidobacterium breve, Bifidobacterium subtilis, Escherichia coli* and strains of the genera including *Bacillus, Bacteroides, Enterococcus* (e.g., *Enterococcus faecium*) and *Leuconostoc*, and mixtures and/or combinations thereof.

Minerals, metals and/or elements: Non-limiting examples of minerals, metals, and elements useful in the systems of the present invention include: zinc, iron, calcium, iodine, copper and selenium. When present, the minerals, metals and/or elements can be on or in a suitable carrier, and comprise from about 1% to about 50% by weight and alternatively from about 2% to about 30%, by weight of the composition comprising the mineral, metal or element and the carrier.

In another example, the active can be a gastrointestinal active. Non-limiting examples of gastrointestingal actives can include anti-diarrheal actives, laxatives, anti-nausea and anti-emetic actives, anti-flattulents, proton pump inhibitors, anti-inflammatory gastrointestinal actives, rafting agents, and combinations thereof.

Non-limiting examples of anti-diarrheal actives can include loperamide, bismuth-containing compositions, bismuth subsalicylate, colloidal bismuth subcitrate, bismuth subcitrate, kaolin, pectin, clays such as attapulgite, activated charcoal, and combinations thereof.

Non-limiting examples of laxatives can include fiber, resistant starch, resistant maltodextrin, pectin, cellulose, modified cellulose, polycarophil, senna, sennosides, bisacodyl, sodium phosphate, docusate, magnesium citrate, mineral oil, glycerin, aloe, castor oil, magnesium hydroxide, and combinations thereof.

Non-limiting examples of anti-nausea and anti-emetic actives can bismuth containing compositions including bismuth subsalicylate, phosphated carbohydrates, diphenhydramine, cyclizine, meclizine, and combinations thereof; non-limiting examples of antacids can include sodium bicarbonate, sodium carbonate, calcium carbonate, magnesium carbonate, magnesium hydroxide, aluminum hydroxide, magnesium silicates, alginic acids, sodium alginate, magaldrate, and combinations thereof.

Non-limiting examples of anti-flattulents can include simethicone, activated charcoal, lactase, alpha-galactosidase enzymes, and combinations thereof; non-limiting examples of H2 receptor antagonists can include famotidine, ranitidine, ciemtidine, nitazidine, and combinations thereof.

Non-limiting examples of proton pump inhibitors can include omeprazole, lansoprazole, esomeprazole, pantoprazole, rabeprazole, and combinations thereof.

A non-limiting example of an anti-inflammatory gastrointestinal active can include mesalamine.

Non-limiting examples of rafting agents can include alginates, pectins and polysaccharides.

Assay for Taste Receptors

Human fungiform taste bud cells were isolated from tongues of humans as described in Ozdener, Mehmet, and Nancy Rawson. "Primary Culture of Mammalian Taste Epithelium." *Methods in Molecular Biology;* 2013; 945: 95-107.

Then the cells were further cultured according to the following procedure. The cells were grown in a Corning® cell culture flask, with a surface area of 75 cm$^2$, a canted neck, and a 0.2 µm Vent cap (Catalog #430641, available from VWR International, Bridgeport, N.J., USA) at 37° C. using a growth medium containing 500 mL of Iscove's Modified Dulbecco's Media (IMDM), 100 mL of Ham's F12 Nutrient Mixture, 60 mL Fetal Bovine Serum (FBS), and 150 µg/mL Penicillin-Streptomycin cocktail (all growth media components available from Life Technologies, Grand Island, N.Y., USA).

After the cells reach 80-90% confluence, which generally takes about seven days of cultivation, the cells were released by adding 3 mL of Gibco® Trypsin-EDTA (0.05%) solution (available from Life Technologies) at 37° C. in couple of minutes, followed by adding 12 mL of cell growth medium to deactivate trypsin. Then the cells were diluted in the growth medium at approximately 250,000 cells/mL. Next, 100 µl volume of cell suspension containing 20,000 to 30,000 cells were seeded into each well of a Falcon® 96 Well Black with Clear Flat Bottom TC-Treated Imaging Plate (REF #353219, available from VWR International, Bridgeport, N.J., USA) and the cells are grown overnight.

After the overnight cultivation, the cell culture media was removed by aspiration. Then, 100 µL of Calcium-6QF solution was added to each well. The Calcium-6QF solution was made by dissolving the contents of one vial of Calcium-6QF (available from Molecular Devices, Sunnyvale, Calif., USA) in 20 mL of assay buffer, which contains Hank's Balanced Salt Solution (HBSS) with 20 mM HEPES (4-(2-hydroxyethyl)-1-piperazineethanesulfonic acid) (both components are available from Life Technologies). The plate was then incubated at 37° C. for 105 min and at room temperature for 15 min. Then the 96-well plate is placed in a FLIPR® Tetra High Throughput Cellular Screening System (available from Molecular Devices) and 20 µL of working solution, as described below, are added to each well. The fluorescence signal was read continuously for 5 min, where the excitation and emission wave lengths used were 488 nM and 510 nM respectively. The peak value and/or area under the curve after five minutes was calculated and recorded.

In order to form the working solution, the test material was diluted with the assay buffer. Examples of test materials can include, but are not limited to GG solutions, PG solutions, 1,3-PPD solutions, full formulations such as those in Example 4 and 5, and combinations thereof. The amount of assay buffer varies depending on the desired final concentration, which occurs when the test material is in the wells. For example, if the test material is GG, it can be desirable to have a final concentration of 2 mM. Thus, a 12 mM working solution is made and when it is added to the wells, the concentration is further reduced to a final concentration of 2 mM. In another example, in order to make a working solution for Examples 4 and 5, and other full formulations, 1 mL of the example is added to 27 mL of assay buffer to form the working solution and then it is added to the wells for an overall reduction of 162 fold.

While the specification concludes with the claims particularly pointing and distinctly claiming the invention, it is believed that embodiments of the present invention will be better understood from this description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitation on the indicated amounts nor on the accuracy of the measurements. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid medication with reduced bitterness comprising:
   a. a drug active, wherein the drug active is selected from the group consisting of guaifenesin, phenytoin, omeprazole, cetirizine, jambu, acetaminophen, and combinations thereof; and
   b. polyquaternium-2.

2. The liquid medication of claim 1 wherein the drug active comprises guaifenesin.

3. The liquid mediation of claim 2 wherein the drug active further comprises acetaminophen.

4. The liquid medication of claim 1 wherein the medication comprises from 0.01% to 1% of the polyquaternium-2.

5. The liquid medication of claim 1 wherein the medication comprises from 0.03% to 0.3% of the polyquaternium-2.

6. The liquid medication of claim 1 wherein the medication comprises less than 0.2% of the polyquaternium-2.

7. The liquid medication of claim 1 wherein an overall bitterness is reduced by at least 30% as compared to an identical composition without the polyquaternium-2 as determined by the in vitro Assay for Taste Receptors.

8. A liquid medication with reduced bitterness comprising:
   a. a drug active selected from the group consisting of guaifenesin, phenytoin, omeprazole, cetirizine, jambu, acetaminophen, and combinations thereof;
   b. polyquaternium-2;
   wherein an overall bitterness is reduced by at least 40% as compared to an identical composition without the polyquaternium-2 as determined by the in vitro Assay for Taste Receptor.

9. The liquid medication of claim 8 comprising less than 0.5% of the polyquaternium-2.

10. The liquid medication of claim 8 wherein an overall bitterness is reduced by at least 60% as compared to an identical composition without the polyquaternium-2 as determined by the in vitro Assay for Taste Receptors.

11. A dose of liquid medication with reduced bitterness comprising:
    a. at least 200 mg guaifenesin;
    b. from 0.05% to 0.2% of polyquaternium-2;
    wherein a Descriptive Profile Panel of in mouth bitter is reduced by at least 25% as compared to an in mouth bitter of an identical composition without the polyquaternium-2.

12. The dose of liquid medication of claim 11 wherein the medication further comprises from 5% to 40% propylene glycol.

13. The dose of liquid medication of claim 11 wherein a Descriptive Profile Panel of after expectoration is reduced by at least 10% as compared to an after expectoration bitter of an identical composition without the polyquaternium-2.

14. The dose of liquid medication of claim 11 further comprising from 325 mg to 500 mg acetaminophen.

15. The dose of liquid medication of claim 14 further comprising dextromethorphan hydrobromide and phenylephrine.

16. The dose of liquid medication of claim 11 wherein the dose comprises from 15 mL to 50 mL liquid.

* * * * *